US009884332B2

(12) United States Patent
Zhou et al.

(10) Patent No.: US 9,884,332 B2
(45) Date of Patent: Feb. 6, 2018

(54) SPRAYING APPARATUS HAVING WATER AND AIR INTAKES

(75) Inventors: Huasong Zhou, Xiamen (CN); Yangfeng Ji, Xiamen (CN); Yongbin Cao, Xiamen (CN); Bin Chen, Xiamen (CN)

(73) Assignees: XIAMEN SOLEX HIGH-TECH INDUSTRIES CO., LTD., Xiamen (CN); Huasong Zhou, Xiamen (CN)

( * ) Notice: Subject to any disclaimer, the term of this patent is extended or adjusted under 35 U.S.C. 154(b) by 179 days.

(21) Appl. No.: 14/122,521

(22) PCT Filed: Jun. 20, 2012

(86) PCT No.: PCT/CN2012/077208
§ 371 (c)(1),
(2), (4) Date: Nov. 26, 2013

(87) PCT Pub. No.: WO2013/000370
PCT Pub. Date: Jan. 3, 2013

(65) Prior Publication Data

US 2014/0091160 A1 Apr. 3, 2014

(30) Foreign Application Priority Data

Jun. 28, 2011 (CN) .......................... 2011 1 0178685

(51) Int. Cl.
*A61M 11/06* (2006.01)
*B05B 7/04* (2006.01)
*A61M 11/00* (2006.01)

(52) U.S. Cl.
CPC ........... *B05B 7/0483* (2013.01); *A61M 11/06* (2013.01); *B05B 7/0425* (2013.01); *A61M 11/002* (2014.02)

(58) Field of Classification Search
CPC ....... B05B 7/04; B05B 7/0483; B05B 7/0425; A61M 11/06; A61M 11/002
(Continued)

(56) References Cited

U.S. PATENT DOCUMENTS 2,388,508 A * 11/1945 Morris .......................... 261/116
2,707,624 A * 5/1955 Shames ................... E03C 1/084 210/460
(Continued)

FOREIGN PATENT DOCUMENTS

CA 2555889 A1 2/2008
CN 2065951 U 11/1990
(Continued)

*Primary Examiner* — Arthur O Hall
*Assistant Examiner* — Chee-Chong Lee
(74) *Attorney, Agent, or Firm* — Rabin & Berdo, P.C.

(57) ABSTRACT

A spraying apparatus includes a convergence chamber having a large end and a small end; at least two water inlets provided in the large end of the convergence chamber, each water inlet having a central axis and the at least two water inlets being arranged at convergent angles to each other so that the central axes converge in free space within the convergence chamber; at least one air intake provided in the convergence chamber between the large end and the small end; and a rectifier opening including a throat provided at the small end of the convergence chamber; and a spraying opening, the rectifier opening having a cross-sectional area that continuously increases outwardly from the throat to the spraying opening, and the throat having a cross-sectional area that is one to three times greater than that of a total cross-sectional area of the at least two water inlets.

12 Claims, 3 Drawing Sheets

(58) Field of Classification Search
USPC .................................................. 239/428–432
See application file for complete search history.

(56) References Cited

U.S. PATENT DOCUMENTS

| | | | | | |
|---|---|---|---|---|---|
| 2,889,999 | A | * | 6/1959 | Tomlinson | E03C 1/084 239/428.5 |
| 3,633,824 | A | * | 1/1972 | Aghnides | 239/428.5 |
| 3,701,482 | A | * | 10/1972 | Sachnik | 239/590.3 |
| 3,708,125 | A | * | 1/1973 | Patterson | 239/428.5 |
| 3,816,065 | A | * | 6/1974 | Marietta | 432/183 |
| 3,938,738 | A | * | 2/1976 | Nagel et al. | 239/9 |
| 4,762,277 | A | * | 8/1988 | Pater et al. | 239/99 |

FOREIGN PATENT DOCUMENTS

| | | | |
|---|---|---|---|
| CN | 2759610 | Y | 2/2006 |
| CN | 101954325 | A | 1/2011 |
| CN | 102366738 | A | 3/2012 |
| CN | 202174021 | U | 3/2012 |
| JP | 2002102100 | A | 4/2002 |

* cited by examiner

SPRAYING APPARATUS HAVING WATER AND AIR INTAKES

BACKGROUND OF THE INVENTION

1. Field of the Invention

The present invention relates to an outlet component for liquid spraying, especially to an air-intake and focused-type spraying apparatus.

2. Background of the Related Art

In some situations, such as when showering or cleaning, a spraying apparatus is needed to apply the liquid. Such a spraying apparatus is used to discharge the liquid from the waterway, with a spraying effect, such as to provide a large spraying area.

How the liquid is diffused is important. One conventional method is to apply the liquid with a shower head, which is simple structurally and easily operated, but there is a disadvantage. The liquid flow is only rectified to spray so that the spraying effect is weak.

Thus, there is a need for a simple apparatus to discharge liquid with a large spraying area, preferably with a good sprayed water particle effect and water saving.

SUMMARY OF THE INVENTION

For spraying a large area, the present invention is provided with an air-intake and focused-type sprayer apparatus, the technical proposal of which follows.

Air-intake and focused-type sprayer apparatus, wherein comprising: a convergence chamber, having along the axial direction thereof a large end and a small end, an inner wall of the large end and the small end is provided with gradual transition; at least two water inlets, which are in communication with the large end of the convergence chamber; all of the water inlets converge within the convergence chamber towards a water discharging direction of the convergence chamber; at least one air intake passage in communication with the convergence chamber from the external open space; and a rectifier opening in communication with the small end of the convergence chamber, the rectifier opening being provided with a throat for allowing water flow to form a liquid seal, the cross-sectional area of the throat is one to three times greater in size than the maximum total cross-section area of the water inlet; the rectifier opening gradually increases outwards in the cross-section size thereof from the throat.

In another preferred embodiment, the cross sections of the convergence chamber, the rectifier opening and the throat have a circular shaped, and the three are rotationally symmetric.

In another preferred embodiment, the convergence chamber has a frustoconical shape.

In another preferred embodiment, the connections of the water inlets and the convergence chamber are rotationally symmetric about the central axis of the convergence chamber.

In another preferred embodiment, the rectifier opening has a frustoconical shape.

In another preferred embodiment, the frustoconical shaped convergence chamber becomes smaller from top to bottom, and the furstoconical shaped rectifier opening becomes larger from top to bottom.

In another preferred embodiment, the apparatus comprises two water inlets and two air intake passages. The two water inlets and the two air intake passages are symmetrically arranged about the central axis of the convergence chamber. The convergence chamber, the rectifier opening and the air intake passages are forming half-to-half respectively in a left set block and a right set block; the left set block and the right set block are contacted tightly.

In another preferred embodiment, the outline of the surface of the left set block and the right set block when coupled to each other is rectangular. The outlets of the water inlets are in the same side of the rectangle while the outlets of the rectifier opening and the air intake passages are in the opposite side to the water inlets.

In another preferred embodiment, the water inlets are in the left set block while the convergence chamber, the rectifier opening and the air intake passages have equal volume in the left set block and the right set block.

The advantages of the present invention are as follows.

1. In tandem with the throat, which is capable of forming a liquid seal, and with the air intake passages, the convergence chamber has a gradual transition between the large and small ends which allows water flow to converge within the convergence chamber, thus augmenting collision between the air and the water flow, and providing an improved effect and increased range of the spraying water particles discharged.

2. The rectifier opening gradually increases outwardly in the cross-sectional size thereof, so that the water-air mixture from the convergence chamber is rectified and flows out with viscosity to the inner wall to become a regular splash bounded by the cross section of the rectifier opening, making it spray uniformly.

3. It can be formed with set blocks thus making it easy to assemble onto various kinds of waterways. It has a small size, few components, and a solid construction.

BRIEF DESCRIPTION OF THE DRAWINGS

The present invention will be further described with the drawings and the embodiments.

DETAILED DESCRIPTION OF THE INVENTION

The First Embodiment

Figure 1:
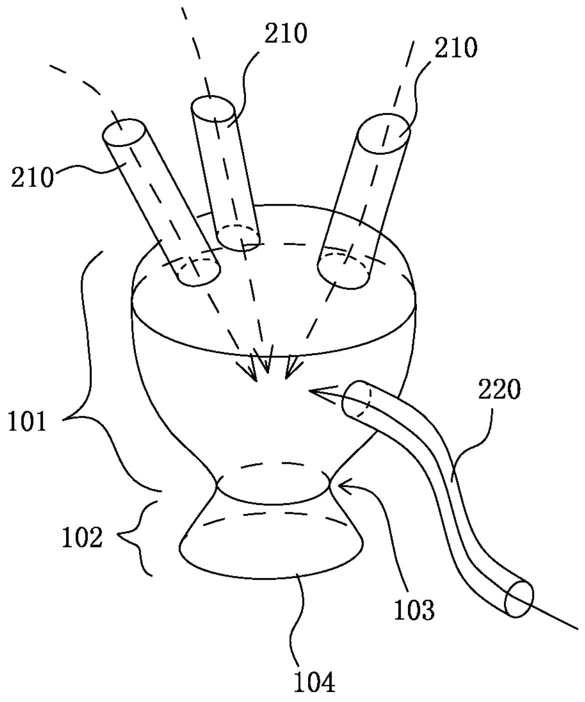
FIG. 1 is a schematic diagram of a first embodiment of the present invention.

As schematically illustrated in FIG. 1, disclosed is an air-intake and focused-type sprayer apparatus, in which a convergence chamber 101 and a rectifier opening 102 are connected and have smooth inner surfaces. The convergence chamber 101 has a large end in an upper portion and a small end in a lower portion along the axial direction. An inner wall is disposed with gradual transition between the large end and the small end. The rectifier opening 102 is provided with a throat 103 where the rectifier opening 102 is connected to the convergence chamber 101. The cross-sectional area of the throat 103 is one to three times greater in size than the maximum total cross-section area of the water inlet path 210. The throat 103 gradually increases towards a spraying opening 104.

The present invention is shown with three water inlets 210. The inlets thereof are disposed in the front of the large end of the convergence chamber 101. The extension lines of the three water inlet paths 210 inside the convergence chamber, or the water flowing paths of the water inlet paths 210, intersect inside the convergence chamber. This structure is very important, so that the water from the water inlets paths impact inside the convergence chamber.

In this embodiment, the cross sections of the convergence chamber 101, the rectifier opening 102 and the throat 103 have a circular shape, and the three are rotationally symmetric. The convergence chamber 101 has a cavity that has a frustoconical shape. The rectifier opening 102 has a frustoconical shape. The connections of the water inlet paths 210 and the convergence chamber 101 are rotationally symmetric about the central axis of the convergence chamber.

An air intake passage 220 is disposed in a side wall of the convergence chamber 101 from the external open space so that air can freely enter into the convergence chamber 101. Water from the water inlets 210 impacts inside the convergence chamber 101 and then flows to the throat 103. Due to the shape of the convergence chamber 101, the cross section of the water in the throat 103 decreases so that the water flow speeds up and forms a liquid seal in the throat 103. Air from the air intake passages 220 mixes with the water thus making the mixture expand so that the impact of the water and the air is increased. Finally, the mixture sprays out from the spraying opening 104 at the end of the rectifier opening 102. Water flows out with viscosity along the inner wall of the rectifier opening 102 to become a regular splash bounded by the inner wall of the rectifier opening thus making it spray uniformly. Meanwhile, the augmented collision enhances inside the inner wall of the rectifier opening 102 thus allowing for a more uniform water air-mixture.

The Second Embodiment

Figure 2:
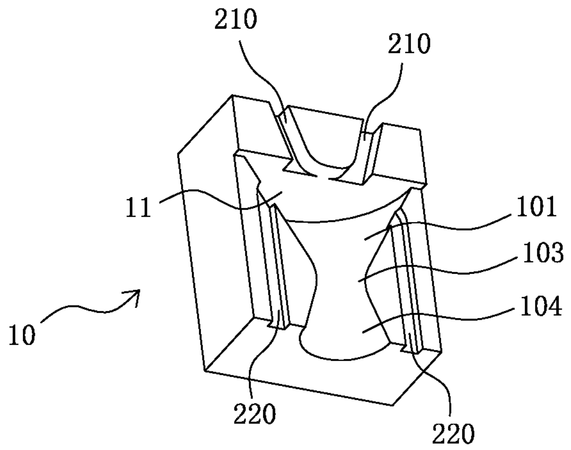
FIG. 2 is a schematic diagram of the right set block of a second embodiment of the present invention.
Figure 3:
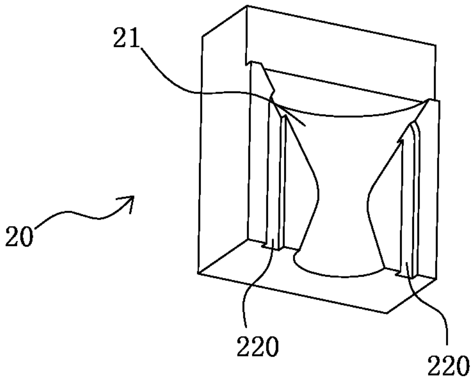
FIG. 3 is a schematic diagram of the left set block of the second embodiment of the present invention.
Figure 4:
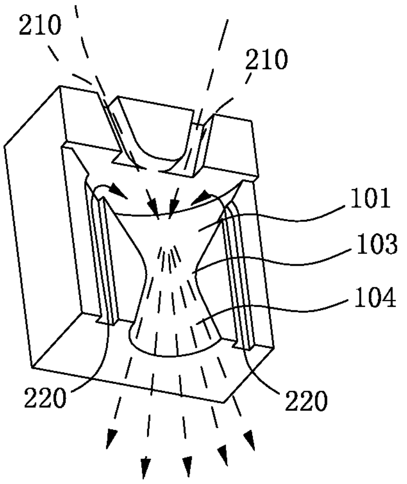
FIG. 4 is a schematic diagram of the waterway of the second embodiment of the present invention.

As shown in FIG. 2, FIG. 3 and FIG. 4, disclosed is another embodiment of the air-intake and focused-type sprayer apparatus. The body of the air-intake and focused-type sprayer apparatus comprises a left set block 10 and a right set block 20, which have rectangular contact surfaces. The two set blocks contact tightly to become a hexahedron. The left set block 10 has two water inlets 210, which have a groove shape formed in the left set block 10. The upper set block 10 has disposed therein an upper cavity 11, which is divided into three sections respectively disposed as half of the convergence chamber 101, the throat 103 and the rectifier opening 104. The side wall of the convergence chamber 101 has two symmetric air intakes 220, which have a groove shape and are formed in the left set block 10 as well.

Correspondingly, the right set block 21 has a lower cavity 21, which is coupled to the upper cavity 11 to form the complete convergence chamber 101. The throat 103 and the rectifier opening 104, and the tight set block 20 has air intake passages 220 the same as the left set block 10. When the two set blocks contact tightly, the air intake passages 220 are formed. The air intake passages 220 and the outlet of the rectifier opening 103, with respect to the outlet of the water inlet paths 210, are respectively formed in the opposite side of the rectangle.

In the second embodiment, the water inlets 210, the convergence chamber 101, the throat 103, the rectifier opening 104, the air intake passage 220 are rotationally symmetric. They have equal volume in the left set block 10 and the right set block 20. The convergence chamber 101 and the rectifier opening 103 have a frustoconical shape. Water from the water inlets 210 enters into the convergence chamber 101 and forms a liquid seal in the throat 103 and, with air from the air intake passage 220, finally sprays out from the rectifier opening 104 with a viscosity to the inner wall. The set blocks type enables fewer components and a tight structure, is easy to assemble onto various waterways and to arrange in an array.

Although the present invention has been described with reference to the preferred embodiments thereof for carrying out the invention, it will be apparent to those skilled in the art that a variety of modifications and changes may be made without departing from the scope of the invention which is intended to be defined by the appended claims.

INDUSTRIAL APPLICABILITY

The present invention provides an air-intake and focused-type sprayer apparatus including a convergence chamber having a large end and a small end. An inner wall of the large end and the small end is provided with a gradual transition. Thus, in tandem with a throat capable of forming the liquid seal and with the air intake passage, the convergence chamber has a gradual transition between the large and small ends thereof that allows water flow to converge within the convergence chamber. Collision between the air and water flow is augmented, and provides an improved effect and increased range of the sprayed water particles discharged, so that the present invention has good industrial applicability.

The invention claimed is:

1. A spraying apparatus having water and air intakes, comprising:

a convergence chamber having, along a central axis thereof, a large end and a small end, and inner walls that have a continuous transition between the large end and the small end;

at least two water inlets provided in the large end of the convergence chamber in communication therewith, each water inlet of the at least two water inlets having a central axis and the at least two water inlets being arranged at convergent angles to each other so that the central axes converge in free space within the convergence chamber towards the small end thereof;

at least one air intake provided in the convergence chamber between the large end and the small end and in communication with the convergence chamber; and a rectifier opening including a throat provided at, and in communication with, the small end of the convergence chamber; and a spraying opening terminating the rectifier opening, the rectifier opening having a cross-sectional area that continuously increases outwardly from the throat to the spraying opening, and the throat being configured to allow water flow to form a liquid seal and having a cross-sectional area that is one to three times greater than that of a total cross-sectional area of the at least two water inlets.

2. The spraying apparatus according to claim 1, wherein the convergence chamber, the rectifier opening, and the throat each have cross-sectional areas that have a circular shape and are rotationally symmetric with one another about the central axis of the convergence chamber.

3. The spraying apparatus according to claim 2, wherein the convergence chamber has a frustoconical shape.

4. The spraying apparatus according to claim 3, wherein the at least two water inlets and the convergence chamber are rotationally symmetric about the central axis of the convergence chamber.

5. The spraying apparatus according to claim 4, wherein the rectifier opening has a frustoconical shape.

6. The spraying apparatus according to claim 5, wherein the convergence chamber having the frustoconical shape becomes smaller from the large end to the small end thereof and the rectifier opening having the frustoconical shape becomes larger from the throat to the spraying opening thereof.

7. The spraying apparatus according to claim 6, wherein the at least two water inlets and two air intakes are symmetrically arranged about the central axis of the convergence chamber, wherein the convergence chamber, the rectifier opening and the two air intakes are formed half-and-half respectively in a left set block and a right set block, and wherein the left set block and the right set block are in close interfacial contact with one another.

8. The spraying apparatus according to claim 7, wherein the left set block and the right set block have respective interfacial surfaces that are coupled to each other to define a rectangle; wherein each of the at least two water inlets are provided in one set block from among the left set block and the right set block, and wherein the rectifier opening and the two air intakes are provided in another set block from among the left set block and the right set block.

9. The spraying apparatus according to claim 8, wherein the at least two water inlets are provided in the left set block; and wherein the convergence chamber, the rectifier opening and the two air intakes have equal volume in the left set block and in the right set block.

10. A spraying apparatus having water and air intakes, comprising:

a convergence chamber having, along a central axis thereof, a large end and a small end, and inner walls that have a continuous transition between the large end and the small end;

at least two water inlets provided in the large end of the convergence chamber in communication therewith, each water inlet of the at least two water inlets having a central axis and the at least two water inlets being arranged at convergent angles to each other so that the central axes converge in free space within the convergence chamber towards the small end thereof;

two air intakes provided in the convergence chamber between the large end and the small end and in communication with the convergence chamber; and a rectifier opening including a throat provided at, and in communication with, the small end of the convergence chamber; and a spraying opening terminating the rectifier opening, the rectifier opening having a cross-sectional area that continuously increases outwardly from the throat to the spraying opening, and the throat being configured to allow water flow to form a liquid seal and having a cross-sectional area that is one to three times greater than that of a total cross-sectional area of the at least two water inlets, wherein the two air intakes and the at least two water inlets are symmetrically arranged about the central axis of the convergence chamber, and wherein the convergence chamber, the rectifier opening and the two air intakes are formed half-and-half respectively in a left set block and a right set block; the left set block and the right set block being in close interfacial contact with one another.

11. The spraying apparatus according to claim 10, wherein the left set block and the right set block have respective interfacial surfaces that are coupled to each other and share a rectangular outline, wherein the at least two water inlets are provided in one set block from among the left set block and the right set block, and wherein the rectifier opening and the two air intakes are provided in another set block from among the left set block and the right set block.

12. The spraying apparatus according to claim 11, wherein the at least two water inlets are positioned in the left set block, and wherein the convergence chamber, the rectifier opening and the two air intakes have equal volume in the left set block and in the right set block.

* * * * *